United States Patent [19]
Takasuka et al.

[11] Patent Number: 5,858,923
[45] Date of Patent: Jan. 12, 1999

[54] HEXAHYDROPYRIDAZINE DERIVATIVE AND HERBICIDE CONTAINING THE SAME AS ACTIVE INGREDIENT

[75] Inventors: Kiyoshi Takasuka; Hideyo Fujii; Seigo Koura; Noriyoshi Katsuyama, all of Tokyo, Japan; Yukiyo Shigeno, Asaka, Japan

[73] Assignee: Agro-Kanesho Co., Ltd., Tokyo, Japan

[21] Appl. No.: 878,962

[22] Filed: Jun. 19, 1997

[51] Int. Cl.⁶ .......................... G07D 237/02; A01N 47/38
[52] U.S. Cl. ............................. 504/236; 544/224
[58] Field of Search ............................ 544/224; 204/236

[56] References Cited

FOREIGN PATENT DOCUMENTS

| | | |
|---|---|---|
| 53-40785 | 4/1978 | Japan . |
| 59-82372 | 5/1984 | Japan . |
| 8-253455 | 10/1996 | Japan . |

*Primary Examiner*—Mukund J. Shah
*Assistant Examiner*—Bruck Kifle
*Attorney, Agent, or Firm*—Oblon, Spivak, McClelland, Maier & Neustadt, P.C.

[57] ABSTRACT

The present invention provides a hexahydropyridazine derivative of the formula (I):

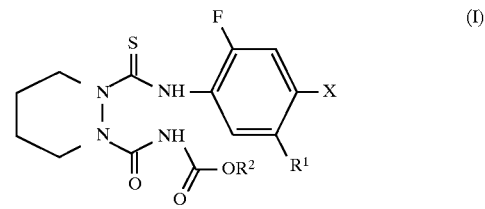

wherein $R^1$ represents an alkynyloxy group, a cycloalkoxy group or an alkoxycarbonylalkylthio group, $R^2$ represents an alkyl group, a phenyl group or a benzyl group, and X represents a halogen atom. This compound exhibits an excellent herbicidal effect on various weeds in treatment of field soil, foliage treatment and flooding treatment of paddy field, and has an excellent selectivity toward the weeds but not the crop.

20 Claims, No Drawings

HEXAHYDROPYRIDAZINE DERIVATIVE AND HERBICIDE CONTAINING THE SAME AS ACTIVE INGREDIENT

BACKGROUND OF THE INVENTION

The present invention relates to a new tetrahydropyridazine derivative and a herbicide containing it as the active ingredient.

It has been known hitherto that some tetrahydropyridazine derivatives have a herbicidal effect. For example, Japanese Patent Unexamined Published Application (hereinafter referred to as "J. P. KOKAI") No. Sho 53-40785 discloses that N-substituted hydrazine derivatives having a structure represented by the following formula have a herbicidal effect:

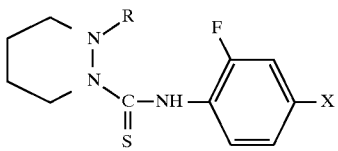

wherein R represents a hydrogen atom or carboethoxy group, and X represents a chlorine atom or bromine atom.

J. P. KOKAI No. Sho 59-82372 discloses that hexa hydropyridazinecarboxylic acid derivatives represented by the following formula have a herbicidal effect:

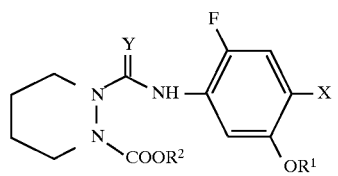

wherein X represents a chlorine atom or bromine atom, Y represents an oxygen atom or sulfur atom, $R^1$ represents a lower alkyl group, lower alkenyl group or lower alkynyl group, and $R^2$ represents a lower alkyl group.

However, these compounds were not always satisfactory in fact, since their herbicidal effect was insufficient and, therefore, they had to be used in a large amount, and the safety of them for crops was insufficient.

SUMMARY OF THE INVENTION

After intensive investigations made under these circumstances, the inventors have found that tetrahydropyridazine derivatives (hereinafter referred to as "the present compound") of the following formula (I) have excellent herbicidal effects, and the present invention has been completed on the basis of this finding:

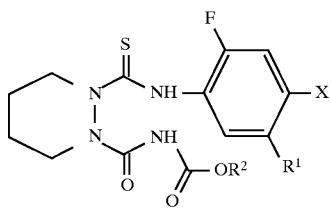

wherein $R^1$ represents an alkynyloxy group, a cycloalkoxy group or an alkoxycarbonylalkylthio group, $R^2$ represents an alkyl group, a phenyl group or a benzyl group, and X represents a halogen atom.

DESCRIPTION OF THE PREFERRED EMBODIMENTS

The detailed description will be given on the present invention.

$R^1$ in the formula (I) represents an alkynyloxy group, a cycloalkoxy group or an alkoxycarbonylalkylthio group.

The alkynyl group in the alkynyloxy group may be either substituted or unsubstituted. The unsubstituted alkynyl groups include, for example, those having 2 to 8 carbon atoms, preferably 2 to 3 carbon atoms. Examples of the unsubstituted alkynyl groups include acetylene, propynyl, butynyl, pentynyl, hexynyl, heptynyl and octynyl groups. The substituents of the alkynyl groups include, for example, alkyl groups having 1 to 5 carbon atoms, hydroxyl group, halogen atoms (such an fluorine, chlorine and bromine atoms), nitro group, cyano group, amino group and imino group. The subutituents are preferably alkyl groups such as methyl and ethyl groups.

The cycloalkyl groups in the cycloalkoxy groups may be either substituted or unsubstituted. The unsubstituted cycloalkyl groups include, for example, alicyclic alkyl groups having 3 to 8 carbon atoms, preferably 5 to 6 carbon atoms. Examples of then include cyclopropyl, cyclobutyl, cyclopentyl, cyclohexyl and cycloheptyl groups. The range of the substituents of the substituted cycloalkyl groups is the same as that of the above-described alkynyloxy groups.

The alkoxyl groups in the alkoxycarbonylalkylthio groups may be either substituted or unsubstituted. The alkoxyl groups may also be cycloalioxyl groups. The unsubstituted alkoxyl groups are those having, for example, 1 to 12 carbon atoms, and preferably 1 to 5 carbon atoms. Examples of the alkoxy groups include methoxy, ethoxy, propoxy, butoxy, pentyloxy, hexyloxy, heptyloxy, octyloxy and nonyloxy groups. The range of the cycloalkoxy groups is the same as that of the above-mentioned one for the case wherein $R^1$ represents the cycloalkoxyl group. The range of the substituents of the substituted alkoxyl groups is the same as that of the above-described alkynyloxy groups.

The alkyl groups in the alkoxycarbonylalkylthio groups may be either substituted or unsubetituted. The unsubstituted alkyl groups are those having, for example, 1 to 6 carbon atoms, and preferably 1 to 3 carbon atoms. Examples of the alkyl groups include methyl, ethyl, propyl and butyl groups. The range of the substituents of the substituted alkyl groups is the same as that of the above-described alkynyloxy groups.

$R^2$ represents an alkyl, a phenyl or a benzyl group.

The term "alkyl group" herein indicates those having 1 to 15, preferably 1 to 9 carbon atoms. The alkyl groups may be either substituted or unsubstituted. The unsubstituted alkyl groups include, for example, methyl, ethyl, propyl, butyl, pentyl, hexyl, heptyl, octyl, nonyl, decyl, undecyl, dodecyl and tridecyl groups. On the other hand, the range of the subutituents of the substituted alkyl groups is the same as that of the above-described alkynyloxy groups.

The term "phenyl group" include also substituted phenyl groups. The range of the substituents of the substituted phenyl groups is the same as that of the above-described alkynyloxy groups. The number of the substituents may be one or more.

Also the term "benzyl group" include also substituted benzyl groups. The range of the substituents of the substituted phenyl groups is the same an that of the above-described alkynyloxy groups.

X represents a halogen atom. The halogen atom is, for example, fluorine, chlorine, bromine or iodine atom. Preferred halogen atom is chlorine or bromine.

The compounds of the present invention can be produced by reacting, for example, a compound of the formula (II):

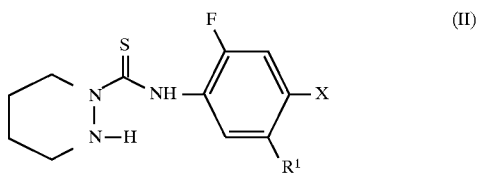

wherein $R^1$ represents an alkynyloxy, a cycloalkoxyl or an alkoxycarbonylalkylthio group, and x represents a halogen atom with a compound of the formula (III):

wherein $R^2$ represents an alkyl, a phenyl or a benzyl group.

The compounds of the formula (II) are known compounds, and they can be easily produced by, for example, a method described in J. P. KOKAI No. Sho 59-70672. The compounds of the formula (III) are also known compounds, and they can be produced by, for example, a method described in Tetrahedron, 31:2007-2014 (1975).

The above-described reaction is usually conducted without any solvent or in a solvent at a reaction temperature of usually −20° to 150° C., preferably −10° to 100° C. for a period of usually 0.1 to 12 hours, preferably 0.5 to 3 hours. When the compound of the formula (II) is used in an amount of 1 equivalent, the compound of the formula (III) is used in an amount of 1 to 2 equivalents, preferably 1 to 1.2 equivalents.

The solvents used for the above-described reaction are inert solvents including aromatic hydrocarbons such an toluene; halogenated hydrocarbons such as chloroform and dichloromethane; ethers such as 1,4-dioxane and tetrahydrofuran; ketones such as acetone and ethyl methyl ketones acetonitrile dimethyl sulfoxide; and N,N-dimethylformamide.

After the completion of the reaction, the reaction liquid is distilled. If necessary, the product may be purified by the recrystallization or chromatography.

The present compound exhibits not only the excellent herbicidal effects but also excellent selective herbicidal effects toward the weeds but not toward the main crops. Namely, the present compound exhibits the herbicidal effect on various weeds which disturb the foliage treatment in a field, such as broadleaf weeds including, for example, wild buckwheat, smartweed, common purulane (*Portulaca oleracea*), chickweed (*Stellaria neglecta*), white goosefoot, Japanese white radish, Japanese hedgepareley, shepherd's purse, Joint vetch, oriental senna, Indian mallow, prickly sida, field pansy, cleaver, ivyleaf morningglory, Tall morningglory, small bindweed, Red Dead Mettle, henbit, Jimson weed, nightshade, speedwell, cocklebur, sunflower, sertless chamomi, marigold, Sun Spurge (Wartweed) and spotted spurge; weeds of Gramineae including, for example, barnyard grass, water grass, yellow fox tail, crabgrass, annual bluegrass, meadow foxtail, oat, Johnsongrass, Quackgras (doggrass), downy broml and giant foxtail; and weeds of cyperaceae including, for example, rice flatsedge and nut grass. On the other hand, the present compound has no harmful effect on the main crops such as corns, soybeans, wheats and rice plants. The present compound also exhibits the herbicidal effect on various weeds which disturbs the flooding of a paddy field such as broadleaf weeds including, for example, *Lindernia pyridaria*, *Rotala indica* and *Elatine Trisandra*; weeds of Cyperaceae including, for example, *Cyperus serotinus* and *Eleocharis acicularis*, and *Sagittaria pygnaea*. On the contrary, the present compound scarcely exerts harmful effect on the rice plant.

When the present compound is practically used as an active ingredient for herbicides, it is usually mixed with a solid carrer, solvent, surfactant and other agricultural assistants, to form an emulsion, solution, microcapsules, microemulsion, wettable powder, suspension, granules, water dispersible granules, water-soluble formulation or the like. Such a formulation contains the present compound as an active ingredient in an amount of 0.002 to 80% by weight, preferably 0.01 to 70% by weight.

The solid carriers include fine powders or granules of kaolin, clay, attapulgite clay, bentonite, acid terra alba, pyrophyllite, talc, diatomaceous earth, calcite, walnut shell powder, urea, ammonium sulfate and synthetic silicic acid hydrate. The solvents include aromatic and aliphatic hydrocarbons such as xylene, naphthas, methylnaphthalene, paraffins and machine oil; alcohols such as isopropanol, butanol, propylene glycol, ethylene glycol, cellosolve and carbitol; ketones such an acetone, cyclohexanone and isophorone; vegetable oils much as soybean oil and cotton seed oil dimethyl sulfoxide; N,N-dimethylformamide; N-methyl pyroridone; acetonitrile; and water.

The surfactants used for emulsification, dispersion, wetting, etc. include anionic surfactants such an ligninsulfonates, polynaphthalenesulfonates, alkylsultates, alylsulfonates, alkylarylsulfonates, dialkylsulfosuccinates, polyoxyethylens alkyl ether phosphates, polyoxyetbylene alkylaryl ether sulfates, polyoxyethylene alkylaryl other phosphates, polyoxyethylene alkylaryl ether sulfonates, as well as phosphoric and sulfuric enter salts of polyoxyethylenestyrenated and benzylated phenyl ether; and nonionic surfactants such as polyoxyethylene alkylaryl others, polyoxyethylene fatty acid esters, polyoxyethylene/polyoxypropylene block copolymers, sorbitan fatty acid esters, polyoxyethylenesorbitan fatty acid esters, as well as polyoxyethylenestyrenated and benzylated phenyl ethers. Other formulation assistants include alginic acid salts, polyvinyl alcohols, carboxymethylcellulose, xanthane gum and acidic isopropyl phosphate.

The present compound is usually used in the form of a formulation for the soil treatment before or after the germination of the weeds, foliage treatment or flooding treatment. The soil treatment includes the soil surface treatment, soil mixing treatment, etc. The foliage treatment includes the overall treatment of all the plants and local treatment in which only the weeds are treated so as not to apply the herbicide to the crops.

The further improvement of the herbicidal effect can be expected by using the herbicide with other herbicides. The herbicide can be used in the form of a mixture with insecticides, acaricides, nematocides, fungicides, plant growth regulators, fertilizers, soil improvers, etc.

The present compound is usable as an active ingredient of a herbicide to be used in paddy field, field, orchard, meadow, lawn, forest or non-agricultural land.

When the present compound is used as an active ingredient of a herbicide, the amount thereof varies depending on the weather conditions, type of the formulation, timing of the treatment, method, place, weed to be killed and crop to be obtained and is usually 0.005 to 40 g, preferably 0.01 to 20 g, per are of the land. A predetermined amount of the emulsion concentrate, wettable powder, suspension concentrate or the like is usually diluted with 1 to 10 liters, per are, of water containing, if necessary, an assistant such as a spreader before the treatment. The granules or the like are usually directly used without the dilution. The spreaders include the above-described surfactants as well as polyoxyethylene resin acids, abietic acid salts, dinaphthylmethanedioulfonates and paraffin emulsion.

EXAMPLES

The following Production Examples, Formulation Examples and Test Examples will further illustrate the present invention, which by no means limit the scope of the present invention. Parts in the Formulation Examples are given by weight.

Before the Examples, the compounds produced in the Examples and properties of them are shown in Table 1 given below.

Production Example 1

1.0 g of {2-chloro-4-fluoro-5-[(tetrahydro-pyridazine-1-carbothionyl)-amino]-phenylsulfanyl} acetic acid methyl ester was dissolved in 5 ml of dichloromethane. 0.27 g of methozycarbonyl isocyanate was added dropwise to the solution at room temperature. After stirring for 1 hour, dichloromethane was distilled off to obtain the crude product, which was recrystallized from benzene to obtain 1.04 g of Compound (10) of the present invention.

Production Example 2

1.0 g of {2-chloro-4-fluoro-5-[(tetrahydro-pyridazine-1-carbothionyl)-amino]-phenylsulfanyl} acetic acid methyl ester was dissolved in 5 ml of dichloromethane. 0.30 g of ethosycarbonyl isocyanate was dropped into the solution at room temperature. After stirring for 1 hour, dichloromethane was distilled off to obtain the crude product, which was recrystallized from benzene to obtain 1.05 g of compound (11) of the present invention.

Compounds (1) to (9) and (12) to (18) of the present invention were produced in the same manner as in Production Examples 1 and 2.

FORMULATION EXAMPLES

Formulation Example 1

50 parts of each of Compounds (1) to (18) of the present invention finely pulverized to a particle size of not larger than 10 μm with an atomizer was thoroughly mixed with 3 parts of sodium ligninsulfonate, 2 parts of sodium laurylsulfate, 10 parts of synthetic silicic acid hydrate and 35 parts of clay while pulverizing them, to obtain a wettable powder.

TABLE 1

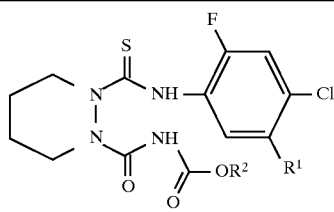

| Compound No. | $R^1$ | $R^2$ | Melting point (°C.) |
|---|---|---|---|
| 1 | $-O-CH_2-C\equiv CH$ | $-CH_3$ | 135.0–142.0 |
| 2 | $-O-CH_2-C\equiv CH$ | $-C_2H_5$ | 158.0–159.0 |
| 3 | $-O-CH_2-C\equiv CH$ | $-CH_3CH_3CH_3$ | 151.0–152.0 |
| 4 | $-O-CH_2-C\equiv CH$ | $-CH(CH_3)_3$ | 160.0–160.5 |
| 5 | $-O-CH_2-C\equiv CH$ | $-CH_3CH_3CH_3CH_3$ | 150.0–151.0 |
| 6 | $-O-CH_2-C\equiv CH$ | $-CH_3CH(CH_3)_2$ | 142.0–143.0 |
| 7 | $-O-CH_2-C\equiv CH$ | phenyl group | 148.0–149.0 |
| 8 | $-O-CH_2-C\equiv CH$ | benzyl group | 125.0–126.0 |
| 9 | cyclopentyloxy group | $-C_2H_5$ | 174.0–175.5 |
| 10 | $-S-CH_2-CO-O-CH_3$ | $-CH_3$ | 138.0–140.0 |
| 11 | $-S-CH_2-CO-O-CH_3$ | $-C_2H_5$ | 138.0–140.0 |
| 12 | $-S-CH_2-CO-O-CH_3$ | $-CH_3CH_3CH_3$ | 139.0–142.0 |
| 13 | $-S-CH_2-CO-O-CH_3$ | $-CH(CH_3)_2$ | 138.0–140.0 |
| 14 | $-S-CH_2-CO-O-CH_3$ | $-CH_2CH_3CH_3CH_3$ | 144.0–145.0 |
| 15 | $-S-CH_2-CO-O-CH_3$ | $-CH(CH_3)CH_3CH_3$ | 140.0–143.0 |
| 16 | $-S-CH_2-CO-O-CH_3$ | $-CH_2CH(CH_3)_3$ | 141.0–142.0 |
| 17 | $-S-CH_2-CO-O-CH_3$ | $-(CH_2)_4-CH_3$ | 136.0–137.0 |
| 18 | $-S-CH_2-CO-O-CH_3$ | $-(CH_2)_7-CH_3$ | 122.0–123.0 |

Formulation Example 2

5 parts of each of Compounds (1) to (18) of the present invention was throughly mixed with 9 parts of polyoxyethylene styryl phenyl other, 6 parts of calcium dodecylbenzenesulfonate and 75 parts of xylene, to obtain an emulsion concentrate.

Formulation Example 3

1 part of each of Compounds (1) to (18) of the present invention finely pulverized to a particle size of not larger than 10 μm with an atomizer was thoroughly mixed with 1 part of synthetic silicic acid hydrate, 2 parts of sodium ligninsulfonate, 30 parts of bentonite and 66 parts of kaolin clay while pulverizing them. The resultant mixture was thoroughly kneaded with water and extruded through a screen with a diameter of 0.8 mm to obtain the granule.

Formulation Example 4

25 parts of each of Compounds (1) to (18) of the present invention finely pulverized to a particle size of not larger than 10 μm with an atomizer was mixed with 3 parts of polyoxyethylene styrenated phenyl ether sulfate, 0.15 part of xanthane gum and 69 parts of water. The resultant mixture was pulverized by a wet mill to a particle size of not larger than 2 μm to obtain a suspension concentrate.

Test on Herbicidal Effect

The following Test Examples will show that the compounds of the present invention are effective as an active ingredient of a herbicide. The present compound is given by the numbers shown in Table 1. The following compounds A and B were used as comparative compounds:

Compound A

Compound A is a compound represented by the following structural formula:

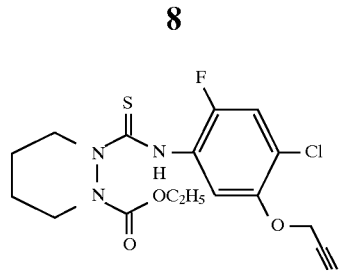

This compound is mentioned in J. P. KOKAI No. Sho 59-82372.

Compound B

Compound B is a compound represented by the following structural formula:

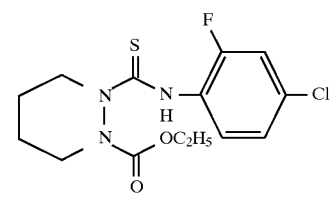

This compound is mentioned in J. P. KOKAI No. Sho 53-40785.

Bioactivity Test Examples

Test Example 1

Pre-emergence soil treatment test

The soil of a field was fed into a 1/5000 are Wagner pot. A predetermined amount of seeds of soybeans (SOY), morningglory (IPO), velvetleaf (ABU), slender amaranth (AMA), common chickweed (STE), corn (COR), rice plant (RIC), Johnsongrass (SOR), barnyardgrass (ECH) or yellow fox tail (SET) were placed on the soil in the pot. The seeds were pressed to level the soil surface, which was then covered with 1.0 cm thick soil. Thereafter, the water dispersible powder of the present compound prepared in the same manner as that of the Preparation Example 1 was diluted to a dose of 1000 ga.i./ha and uniformly applied to the soil with a spray gun. Two weeks thereafter, the germination and growth of the seeds were observed. The results are shown in Table 2. The results were classified into 11 classes ranging from 0 (the same level as untreated weeds) to 10 (the weeds were completely died).

TABLE 2

| Compound No. | Amount (g/ha) | SOY | IPO | ABU | AMA | STE | COR | RIC | SOR | ECH | SET |
|---|---|---|---|---|---|---|---|---|---|---|---|
| 1 | 1000 | 0 | 4 | 7 | 6 | 8 | 8 | 2 | 9 | 8 | 10 |
| 2 | 1000 | 0 | 10 | 10 | 10 | 10 | 10 | 9 | 10 | 10 | 10 |
| 4 | 1000 | 0 | 8 | 10 | 10 | 10 | 3 | 0 | 10 | 10 | 10 |
| 5 | 1000 | 1 | 2 | 10 | 8 | 9 | 3 | 2 | 10 | 8 | 10 |
| 6 | 1000 | 1 | 10 | 10 | 10 | 10 | 4 | 5 | 10 | 9 | 10 |
| 7 | 1000 | 1 | 1 | 2 | 2 | 5 | 4 | 3 | 10 | 9 | 10 |
| 8 | 1000 | 4 | — | 10 | 10 | 5 | 1 | 1 | 10 | 5 | 10 |
| 9 | 1000 | 0 | 2 | 5 | 1 | — | 0 | 0 | 8 | 9 | 9 |
| 10 | 1000 | 0 | 7 | 5 | 6 | 9 | 3 | 1 | 4 | 3 | 3 |
| 11 | 1000 | 0 | 0 | 10 | 10 | 10 | 0 | 0 | 1 | 2 | 2 |
| 13 | 1000 | 0 | 2 | 8 | 8 | 10 | 2 | 1 | 3 | 3 | 3 |
| 14 | 1000 | 0 | 2 | 5 | 6 | 9 | 0 | 0 | 1 | 2 | 2 |
| 15 | 1000 | 0 | 7 | 9 | 9 | 10 | 0 | 0 | 1 | 3 | 3 |
| 16 | 1000 | 0 | 3 | 3 | 5 | 3 | 4 | 2 | 4 | 3 | 8 |
| B | 1000 | 0 | 0 | 2 | 3 | 4 | 0 | 1 | 2 | 3 | 1 |

It is clear from the results given in Table 2 that when the present compound is used for the pre-emergence soil treatment, the excellent herbicidal effect is obtained on the weeds, while the phytotoxic effects on the main cereals, i.e. soybeans (SOY), corn (COR) and rice plant (RIC), were only slight. It is also understood that the present compound has a more excellent selective herbicidal effect toward the weeds than that of Comparative compound B.

Test Example 2
Post-emergence foliar treatment test

The soil of a field was fed into a 1/5000 are Wagner pot. A predetermined amount of seeds of soybeans (SOY), morning glory (IPO), Indian marrow (ADU), slender amaranth (AMA), common chickweed (STE), corn (COR), rice plant (RIC), Johnsongrass (SOR), barnyardgrass (ECH) or yellow foxtail (SET) were placed on the soil in the pot. The seeds were pressed to level the soil surface, which was then covered with 1.0 cm thick soil. After growing in a greenhouse for 10 days, an emulsion of the present compound prepared in the same manner an that of Preparation Example 2 was diluted to a dose of 30 ga.i./ha and uniformly applied to the soil with a spray gun. Two weeks thereafter, the germination and growth of the seeds were observed. The results are shown in Table 3. The results were classified into 11 classes ranging from 0 (the same level as untreated weeds) to 10 (the weeds were completely died).

was 3 cm. The water dispersible powder of the present compound prepared in the same manner as that of Preparation Example 1 was diluted to a concentration of 60 ga.i./ha and a predetermined amount of the herbicide thus obtained was dropped into the water on the next day. After growing in a room, the state of the growing was observed 14 days after the treatment. The results are shown in the following Table 4. The results were classified into 11 classes ranging from 0 (the same level as untreated weeds) to 10 (the weeds were completely died).

TABLE 4

| Compound No. | Amount (g/ha) | Transplanted RICE | EC | RO | EL | CY | SC | MO |
| --- | --- | --- | --- | --- | --- | --- | --- | --- |
| 8 | 60 | 5 | 6 | 10 | 10 | 10 | 10 | 10 |
| 9 | 60 | 1 | 8 | 9 | 9 | 9 | 7 | 9 |
| 10 | 60 | 0 | 6 | 1 | 1 | 0 | 0 | 1 |
| 11 | 60 | 0 | 9 | 8 | 8 | 8 | 8 | 8 |
| 13 | 60 | 0 | 10 | 8 | 8 | 8 | 6 | 7 |
| 14 | 60 | 0 | 9 | 8 | 8 | 7 | 4 | 6 |
| 15 | 60 | 0 | 9 | 10 | 10 | 10 | 8 | 10 |
| 16 | 60 | 0 | 10 | 10 | 10 | 10 | 8 | 10 |
| A | 60 | 8 | 10 | 10 | 10 | 10 | 9 | 10 |
| B | 60 | 1 | 3 | 3 | 2 | 1 | 0 | 1 |

It is clear from the results shown in Table 4 that the present compounds exhibits a strong selective herbicidal effect on the weeds but only a slight phytotoxic effect on the

TABLE 3

| Compound No. | Amount (g/ha) | SOY | IPO | ABU | AMA | STE | COR | RIC | SOR | ECH | SET |
| --- | --- | --- | --- | --- | --- | --- | --- | --- | --- | --- | --- |
| 9 | 30 | 0 | 10 | 10 | 8 | 10 | 0 | 1 | 8 | 3 | 8 |
| 10 | 30 | 2 | 10 | 10 | 10 | 3 | 0 | 5 | 5 | 2 | 9 |
| 11 | 30 | 0 | 10 | 10 | 9 | 10 | 0 | 0 | 2 | 1 | 3 |
| 13 | 30 | 1 | 10 | 10 | 10 | 7 | 0 | 3 | 4 | 2 | 7 |
| 14 | 30 | 0 | 10 | 10 | 9 | 3 | 0 | 0 | 2 | 1 | 3 |
| 15 | 30 | 0 | 10 | 10 | 10 | 9 | 0 | 0 | 5 | 2 | 7 |
| 16 | 30 | 1 | 10 | 10 | 10 | 8 | 0 | 3 | 5 | 3 | 7 |
| A | 30 | 5 | 10 | 10 | 6 | — | 3 | 4 | 6 | 3 | 4 |
| B | 30 | 0 | 1 | 4 | 2 | 1 | 0 | 0 | 1 | 0 | 1 |

It is clear from the results given in Table 3 that when the present compound is used for the foliage treatment in the post-emergence period, the excellent selective herbicidal effect was also obtained on the weeds, while the phytotoxic effects on the main cereals, i.e. soybeans (SOY), corn (COR) and rice plant (RIC), were only slight. It in also understood that the compounds of the present invention have a more excellent selective herbicidal effect toward the weeds than that of comparative compounds A and B as a whole. The phytotoxic effect of comparative compound A on soybeans and corn were stronger than that of the compounds of the present invention.

Test Example 3
Treatment Test of Paddy Field Condition

The soil of a paddy field was fed into a 10 cm×10 cm plastic pot. After plowing, *Panicum Crus-galli var oryzicola* (EC), *Rotala indica* (RO), *Elative friandra* Sehk. var. *japonicus* (EL), *Cyperus difformis* (CY), *Seripus juncoides* Rexb. var. *hotarui Ohwi* (SC) or *Monochoria vagin alis* (MO) were seeded, Seedlings of rice plant of 2.5-foliate stage were planted in the soil and flooded. The water depth transplanted rice plant in the treatment of the sail of the paddy field. It is also understood that the compounds of the present invention have a more excellent selective herbicidal effect toward the weeds than that of comparative compound B and that the phytotoxic effect of these compounds on the transplanted rice plant (RICE) were far lower than that of comparative compound A.

Effect of the Invention

The present compound has an excellent selective herbicidal effects on weeds. Namely, the present compound exhibits an excellent herbicidal effect on various weeds in the treatment of the soil of the field, foliage treatment and flooding treatment of the paddy field, while they exhibit substantially no phytotoxic effect on the main crop. Therefore, the present compound is usable as an active ingredient of herbicides for various purposes.

What is claimed is:

1. A compound of formula (I):

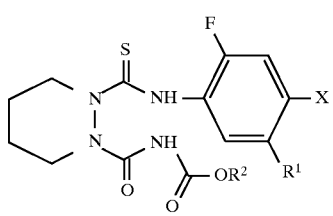

wherein $R^1$ represents a $C_2$–$C_8$ alkynyloxy group, a $C_3$–$C_8$ cycloalkoxy group, and an alkoxycarbonylalkylthio group wherein alkoxy has 1 to 12 carbon atoms and alkyl has 1 to 6 carbon atoms, $R^2$ represents a $C_1$–$C_{15}$ alkyl group, a phenyl group or a benzyl group, and X represents a halogen atom.

2. The compound of claim 1, wherein $R^1$ is an alkoxy carbonylalkylthio group and $R^2$ is an alkyl group.

3. The compound of claim 2, wherein $R^1$ is a methoxy carbonylmethylthio group.

4. The compound of claim 2, wherein $R^2$ is an alkyl group having 1 to 15 carbon atoms.

5. The compound of claim 4, wherein $R^2$ is an alkyl group having 1 to 9 carbon atoms.

6. The compound of claim 1, wherein X is a chlorine or bromine atom.

7. The compound of claim 5 being {5-[2-sec-butoxycarbonyl aminocarbonyl-tetrahydro-pyridazine-1-carbothionyl)-amino]-2-chloro-4-fluorophenyloulfanyl} acetic acid methyl ester.

8. A herbicide comprising the compound of claim 1 as an active ingredient.

9. The herbicide of claim 8, wherein $R^1$ is an alkoxycarbonylalkylthio group and $R^2$ is an alkyl group.

10. The herbicide of claim 9, wherein $R^1$ is a methoxy carbonylmethylthio group.

11. The herbicide of claim 8, wherein $R^2$ is an alkyl group having 1 to 15 carbon atoms.

12. The herbicide of claim 11, wherein $R^2$ is an alkyl group having 1 to 9 carbon atoms.

13. The herbicide of claim 8, wherein X is a chlorine or bromine atom.

14. The herbicide of claim 13, wherein said compound is {5-[2-sec-butoxycarbonylaminocarbonyl-tetrahydropyridazine-1-carbothionyl)-amino]-2-chloro-4-fluorophenylsulfanyl} acetic acid methyl ester.

15. The herbicide of claim 8, wherein the compound in used in a form of an emulsion, a solution, microcapsules, a microemulsion, water dispersible powder, a suspension, granules, water dispersible granules or water-soluble formulation.

16. The herbicide of claim 8, wherein said compound is present in an amount of 0.002 to 80% thereof.

17. A process for producing the compound of claim 1, comprising reacting a compound of the formula (II):

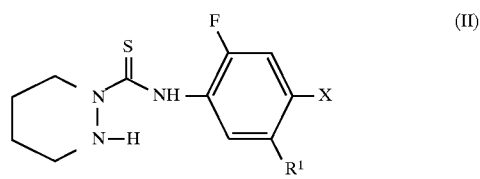

wherein $R^1$ represents a $C_2$–$C_8$ alkynyloxy group, a $C_3$–$C_8$ cycloalkoxy group, and an alkoxycarbonylalkylthio group wherein alkoxy has 1 to 12 carbon atoms and alkyl has 1 to 6 carbon atoms, and X represents a halogen atom, with a compound of the formula (III):

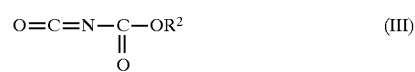

wherein $R^3$ represents a $C_1$–$C_{15}$ alkyl group, a phenyl group or a benzyl group.

18. The process of claim 17, wherein $R^1$ is an alkoxycarbonylalkylthio group, $R^2$ is an alkyl group and X is a chlorine.

19. The process of claim 18, wherein said compound is {5-[2-sec-butoxycarbonyl aminocarbonyl-tetrahydro-pyridazine-1-carbothionyl)-amino]-2-chloro-4-fluoro-phenylsufanyl} acetic acid methyl ester.

20. The process of claim 17, wherein the compound of the formula (II) is reacted with the compound of the formula (III) at −20° to 150° C. for 0.1 to 12 hr. at a ratio of 1 equivalent of the compound (II) to 1 to 2 equivalent of the compound (III).

* * * * *